United States Patent

Pennig

Patent Number: 5,536,127
Date of Patent: Jul. 16, 1996

[54] HEADED SCREW CONSTRUCTION FOR USE IN FIXING THE POSITION OF AN INTRAMEDULLARY NAIL

[76] Inventor: Dietmar Pennig, Hans-Driesch-Strasse 12, 50935 Cologne, Germany

[21] Appl. No.: 392,385

[22] Filed: Feb. 22, 1995

[30] Foreign Application Priority Data

Oct. 13, 1994 [DE] Germany ............................ 9416456 U
Oct. 25, 1994 [DE] Germany ............................ 9417104 U

[51] Int. Cl.⁶ ............................ F16B 35/04; A61B 17/56
[52] U.S. Cl. .............................. 411/413; 411/397; 606/73
[58] Field of Search ...................................... 411/389, 397, 411/412, 413; 606/65, 72, 73

[56] References Cited

U.S. PATENT DOCUMENTS

| | | | |
|---|---|---|---|
| 354,123 | 12/1886 | Flynn | 411/397 |
| 4,463,753 | 8/1984 | Gustilo | 606/73 |
| 5,019,079 | 5/1991 | Ross | 606/73 X |
| 5,259,398 | 11/1993 | Vrespa | 606/73 X |
| 5,375,956 | 12/1994 | Pennig | 411/413 X |

FOREIGN PATENT DOCUMENTS 314950  5/1989  European Pat. Off. ............ 411/413

*Primary Examiner*—Neill R. Wilson
*Attorney, Agent, or Firm*—Hopgood, Calimafde, Kalil & Judlowe

[57] ABSTRACT

The invention relates to a headed screw for fixing an intramedullary nail in position. An external thread on the screw shank is provided over all, or a part of spaced parts, of the length of the shank. The screw head is provided with an external thread having a direction of helical advance which is opposite the direction of helical advance of the screw-shank thread.

9 Claims, 1 Drawing Sheet

HEADED SCREW CONSTRUCTION FOR USE IN FIXING THE POSITION OF AN INTRAMEDULLARY NAIL

RELATED CASE

This application relates to concepts disclosed in my application Ser. No. 08/171,274, filed Dec. 21, 1993, now U.S. Pat. No. 5,375,956, issued Dec. 27, 1994. The disclosure of said application is hereby incorporated by reference.

BACKGROUND OF THE INVENTION

The present invention relates to a headed screw construction wherein the shank of the screw locates in transverse anchor holes of an intramedullary nail and wherein threads on the shank of the screw are adapted for anchorage in bone.

The use of screw threads to fix or to anchor an intramedullary nail is known from EP 306,709 A2. In that case, an elongate screw is threaded for the entire length of its shank and passes through the intramedullary nail.

Screws having a shank with external threads only over a part of their length are known from U.S. Pat. No. 4,463,753. In that case, the two spaced regions of screw threads on the same shank serve to provide a compressive action, bringing together two fracture-separated parts of a bone. Threaded advance for the respective spaced thread regions is in the same direction, but with differing pitch. This prior art screw has no relation to an intramedullary nail.

BRIEF STATEMENT OF THE INVENTION

The object of the present invention is to provide a screw construction for fixing the position of an intramedullary nail, wherein the screw is easily positioned for intramedullary-nail engagement and is easily removable.

The invention achieves this object in a screw construction (a) in which the screw has a headed end which is externally threaded in a first direction of helical advance, and (b) in which the screw has an elongate shank at least a portion of which is externally threaded in the opposite or second direction of helical advance. In one embodiment, the screw shank is threaded for substantially its entire length and is adapted to pass through a bored transverse hole in an intramedullary nail, with proximal and distal portions of the shank thread securing the screw in cortical substance of a bone on both sides of the nail. In another embodiment, a central portion of the screw shank is cylindrical for clean fit to the transverse hole in the nail, and separate threads on the screw shank, proximally of the cylindrical portion and distally of the cylindrical portion, have the same direction of helical advance, as well as the same axial advance per turn of their respective threads. In a third embodiment, the only shank threads are at the distal end of the shank, there being a smooth cylindrical shank surface been the head and the distal-end threads. In any of these embodiments, when the screw is to be removed from its threaded anchorage to bone, an internally threaded nut may be threaded onto the external threads of the head. Once the nut has achieved a limit of head-thread engagement, continued nut rotation in the same direction is operative to drive the shank threads to retract the same from bone engagement. Thus, the screw of the invention can be removed from pinned locating engagement with the intramedullary nail and from threaded engagement to a bone, merely by driving the nut in the direction opposite to the direction of initial shank-screw engagement to the bone.

Admittedly, the retracting direction of screw rotation could also be obtained using an Allen-head wrench, but an Allen-head wrench does not enable a retracting pull to be exerted on the screw. Thus, it is practically impossible to use an Allen-head wrench or a Phillips screwdriver to detach an ingrown screw from bone. The external thread on the screw head does not start at the top of the screw head but, rather, offsets somewhat from the top of the screw head. There is, therefore, a cylindrical feature in the region of the screw head, to facilitate attachment of the internally threaded nut.

Between the bottom of the screw head and the external thread on the screw shank, there is a free space the size of which depends on the size of the screw and the purpose of its use.

DESCRIPTION OF THE DRAWINGS

Illustrative embodiments of the invention will be described in detail, in conjunction with the accompanying drawings, in which.

DETAILED DESCRIPTION OF THE PREFERRED EMBODIMENTS

Figure 1:
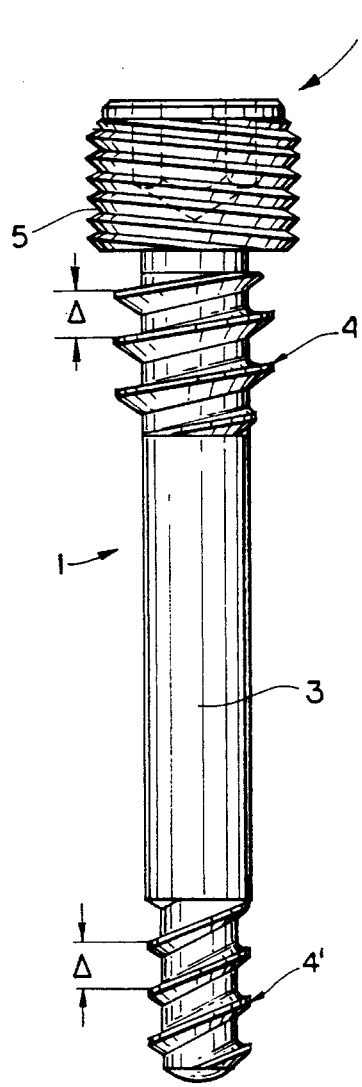
FIG. 1 is an enlarged view in side elevation of a headed-screw construction, illustrating a first embodiment of the invention.

In FIG. 1, a screw 1 of the invention is shown to have a head 2 and a shank 3. A major portion of the screw shank is unthreaded and smoothly cylindrical; a first screw-shank thread 4 is provided in the proximal-end vicinity of the bottom of the screw head 2, and a second screw-shank thread 4' is provided at the distal end of the shank. The maximum diameter of the proximal threads 4 is greater than the diameter of the cylindrical region of the shank, and the maximum diameter of the distal thread 4' is at least no greater than the diameter of the cylindrical portion of the shank. The pitch of both threads 4, 4' is the same, i.e., the axial advance A per turn is the same for both of threads 4, 4'. When using screw 1 to fix the position of an intramedullary nail these screw-shank threads 4, 4' are thread-engaged in cortical substance of the bone, on opposite sides of an intramedullary nail to which the cylindrical portion is fitted.

Figure 2:
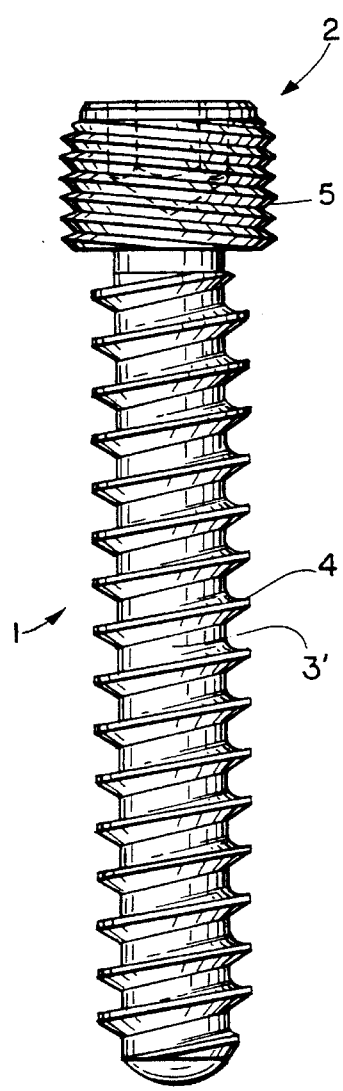
FIG. 2 is a view similar to FIG. 1, to show a second embodiment.

The screw head 2 is shown with a polygonal key or socket formation 9, as for driving engagement by an Allen-head wrench 10 (FIG. 2). But the screw head 2 may be otherwise key-formed as at 11 for driving engagement by other-type drivers, as by a Phillips screwdriver (shown in said U.S. Pat. No. 5,375,956); thus, the screw 1 may be formed for inwardly driven engagement to bone, merely by selection of a suitable wrench or screwdriver.

The outside of the screw head 2 is provided with a screw-head thread 5, the thread-advance of which is directed opposite the direction of thread-advance of the screw-shank thread 4, i.e., one of these threads is a right-hand thread, and the other is a left-hand thread. This being the case, and as disclosed in said co-pending application, an internally threaded tool such as a nut may be threaded onto the head thread 5, to the point of engagement with a stop, such as an internal shoulder formation; once the stop is engaged, continued nut rotation in the same direction is operative to retract screw 1 from the patient's bone. And, if perchance, the threaded shank-to-bone engagement has been so fretted as to make unthreading retraction impossible, the nut will serve as a readily grasped means of directly pulling the screw out of its inadequate engagement to the bone.

In the embodiment of FIG. 2, the shank 3' is threaded for substantially its entire length, and it will be understood that the maximum diameter of the screw threads is such as to derive distributed seating alignment in the transverse bore of an intramedullary nail, with thread engagement to cortical bone on both sides of an engaged intramedullary nail. Head threads 5 may be of the same nature described for FIG. 1, namely, the head threads being in the opposite direction of helical advance, compared to the shank threads.

Figure 3:
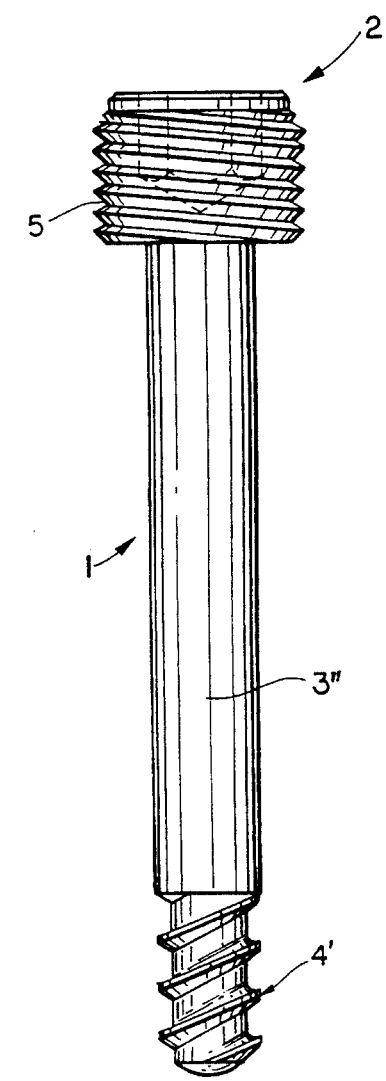
FIG. 3 is another view similar to FIG. 1, to show a third embodiment.

In the embodiment of FIG. 3, the shank 3" is a smooth cylinder for substantially its entire length, and shank threads 4' are limited to the distal end of the shank, it being noted in FIG. 3 that the distal-shank threads 4' have a maximum diameter that does not exceed the cylindrical diameter of the shank. Head threads 5 are again of the same nature as described for FIG. 1, namely, the head threads being in the opposite direction of helical advance, compared to the shank threads.

We claim:

1. A headed screw with a bone-engaging screw thread, comprising an elongate shank having an external thread for bone-engaged anchorage of said screw, and a drive head at one end of said shank, wherein:

(a) the drive head (2) has an external thread (5) having a direction of thread advance which is opposite to the direction of shank-thread advance;

(b) the shank thread is at least at the opposite end of said shank; and (c) the maximum diameter of the shank thread is the maximum diameter of the shank.

2. The headed screw of claim 1, wherein the shank thread at the said opposite end is limited to only a portion of the length of said shank, the remainder of the shank being cylindrical.

3. The headed screw of claim 1, wherein the shank thread extends over substantially the entire length of the shank.

4. A headed screw with a bone-engaging screw thread, comprising an elongate shank having an external thread for bone-engaged anchorage of said screw, and a drive head at one end of said shank, wherein:

(a) the drive head (2) has an external thread (5) having a direction of thread advance which is opposite to the direction of shank-thread advance;

(b) the shank thread is at least at the opposite end of said shank and is limited to only a portion of the length of said shank; and (c) a second threaded portion of said shank is additionally provided near said one end.

5. The headed screw of claim 3, wherein said shank is cylindrical over an intermediate portion, between the respective threaded ends of said shank.

6. A headed screw with a bone-engaging screw thread, comprising an elongate shank having an external thread for bone-engaged anchorage of said screw, and a drive head at one end of said shank, wherein:

(a) the drive head (2) has an external thread (5) having a direction of thread advance which is opposite to the direction of shank-thread advance;

(b) the shank thread is at least at the opposite end of said shank;

(c) a portion of shank is cylindrical; and (d) the thread at the opposite end of said shank has a maximum diameter that is at least no greater than the diameter of said cylindrical portion.

7. The headed screw of claim 6, wherein a second threaded portion is additionally provided, between said cylindrical portion and said head, the threads of said second threaded portion being of greater outside diameter than the diameter of said cylindrical portion.

8. The headed screw of claim 6, wherein a second threaded portion is additionally provided, between said cylindrical portion and said head, the threads of said second threaded portion being of greater outside diameter than the diameter of said cylindrical portion, and the threads of said first threaded portion and of said second threaded portion having the same axial advance per turn.

9. A headed screw with a bone-engaging screw thread, comprising an elongate shank having an external thread for bone-engaged anchorage of said screw, and a drive head at one end of said shank, wherein:

(a) the drive head (2) has an external thread (5) having a direction of thread advance which is opposite to the direction of shank-thread advance;

(b) the shank thread is only at the opposite end of said shank;

(c) the remainder of said shank is cylindrical, and (d) the maximum diameter of the shank thread is no greater than the diameter of said cylindrical remainder.

* * * * *